United States Patent [19]

Whalen et al.

[11] Patent Number: 5,327,341

[45] Date of Patent: Jul. 5, 1994

[54] COMPUTERIZED FILE MAINTENANCE SYSTEM FOR MANAGING MEDICAL RECORDS INCLUDING NARRATIVE REPORTS

[76] Inventors: Edward J. Whalen, 61 Sage Cir., San Ramon, Calif. 94583; Gardener Strong, 22 Olive Ave., Piedmont, Calif. 94611

[21] Appl. No.: 783,133

[22] Filed: Oct. 28, 1991

[51] Int. Cl.5 ............................................. G06F 15/00
[52] U.S. Cl. ........................... 364/413.01; 364/419.07; 364/419.1; 364/419.19
[58] Field of Search ....................... 364/413.01, 419.07, 364/419.1, 419.19; 369/25

[56] References Cited

U.S. PATENT DOCUMENTS 4,315,309  2/1982  Coli ..................................... 364/200
5,146,439  9/1992  Jachmann et al. ..................... 369/25

Primary Examiner—Roy N. Envall, Jr.
Assistant Examiner—Ari M. Bai
Attorney, Agent, or Firm—Bielen, Peterson & Lampe

[57] ABSTRACT

A file maintenance system for computer processing of multiple files of a client/patient type, the files having record sets in an organizational structure combining a plurality of standard, categorical, field-defined records with identified text fields of fixed character length with a plurality of hybrid categorical, extended-field records of virtually unlimited character length with means for editing entered text without reentry of previously entered data in the extended field.

13 Claims, 15 Drawing Sheets

FIG. 3

```
                EXTRACTION FILE DIRECTORY
    ┌─────────────────────────────────────────────┐
    │ 1   ADD A NEW EXTRACTION RECORD.            │
    │ 2   CORRECT OR ADD TO AN EXISTING RECORD.   │
    │ 3   ADD TO OR CORRECT THERAPY REPORT FILES. │
    │ 4   ADD TO OR CORRECT LABORATORY REPORT FILES. │
    │ 5   PRINT A PATIENT REPORT.                 │
    │ 6   LABORATORY NAME FILE MAINTENANCE.       │
    │ 7   KEY WORD FILE MAINTENANCE.              │
    │ 8   LABORATORY HEADER MAINTENANCE.          │
    │ 9   TEST SELECTION FILE MAINTENANCE.        │
    │ 10  EXIT TO MAIN DIRECTORY.                 │
    └─────────────────────────────────────────────┘

SELECT ONE (USE DOWN ARROW) & [CR] TO SELECT.
```

FIG. 4

```
    ┌──────────────────────────────────┐
    │ THE CURRENT PATIENT IS NO. 1     │   JOE SMITH
    │ DO YOU WANT TO USE THIS ONE? (*)Y/N? │   Y
    └──────────────────────────────────┘
```

FIG. 5

```
                    HEADER DIRECTORY
    ┌─────────────────────────────────────────┐
    │  1  PHYSICIAN'S ORDERS:                 │
    │  2  PLANS & REMINDERS:                  │
    │  3  M.D. PROBLEM LIST:                  │
    │  4  KEYWORD LIST:                       │
    │  5  SENSITIVITIES AND INTOLERENCES:     │
    │  6  CURRENT LONG TERM THERAPY:          │
    │  7  DRUG REFILLS:                       │
    │  8  PREVIOUS AND SHORT TERM THERAPY:    │
    │  9  CANCELLED PRESCRIPTIONS:            │
    │ 10  CONSULTANT/REFERRING PHYSICIAN LIST:│
    │ 11  HOSPITALIZATION LIST:               │
    │ 12  PROCEDURE LIST:                     │
    │ 13  FAMILY HISTORY:                     │
    │ 14  HABITS AND EXPOSURES:               │
    │ 15  IMMUNIZATIONS:                      │
    │ 16  INFECTIONS:                         │
    │ 17  SYSTEMIC SYMPTOMS AND DISEASES:     │
    │ 18  PSYCHIATRY:                         │
    │ 19  HEADACHE:                           │
    │ 20  NEUROLOGY:                          │
    │ 21  BACK PAIN:                          │
    │ 22  SKELETAL:                           │
    │ 23  MUSCLES, TENDONS AND BURSAE:        │
    │ 24  EYES:                               │
    │ 25  EARS:                               │
    └─────────────────────────────────────────┘
```

*SEE FIG. 5A*

*SEE FIG. 5*

FIG. 5A

```
26 NOSE:
27 SINUSES:
28 MOUTH:
29 THROAT:
30 RESPIRATORY:
31 CHEST PAIN:
32 CARDIAC:
33 ECG:
34 STRESS TEST:
35 VASCULAR:
36 ABDOMIN:
37 ABDOMINAL PAIN:
38 GASTROINTESTINAL:
39 URINARY TRACT:
40 REPRODUCTIVE:
41 ENDOCRINE:
42 METABOLIC:
43 HEMATOLOGIC:
44 LYMPHATIC:
45 IMMUNOLOGIC:
46 SKIN:
47 SUBCUTANEOUS TISSUE:
48 OTHER CLINICAL FINDINGS:
49 NON-CLINICAL FINDINGS:
50 ISOLATED LABORATORY ABNORMALITIES:
51 PROGRESS NOTES:
52 LABORATORY FLOW SHEETS:
```

SELECT THE CATAGORY FOR REVIEW OR CORRECTION OR [-1] TO STOP    51

PATIENT # 1   JOE SMITH

```
1  HEADER NUMBER  51       PROGRESS NOTES:
2  DATE.                   09/08/91
3  KEYWORD #.  0
```

SELECT ONE OR [CR] TO END OR [/] TO STOP

FIG. 6

```
1                                    1 CTL-C PG DOWN
1                                    1 CTL-R PG UP
1                                    1 CTL-D 1 SP RT
1                                    1 CTL-F 1 WD RT
1                                    1 CTL-S 1 SP LF
1                                    1 CTL-A 1 WD LF
1                                    1 CTL-N END TXT
1                                    1 CTL-O END PG.
1                                    1 CTL-B BGN TXT
1  ┌─────────────────────────────┐   1 CTL-T BGN PG
1  │ THIS RECORD EXISTS BUT IT IS EMPTY. │ 1 CTL-E UP 1 LN
1  │ ENTER YOUR TEXT OR CTL-KX TO STOP. │  1 CTL-X DN 1 LN
1  └─────────────────────────────┘   1 CTL-KB BGN BL
1                                    1 CTL-KK END BL
1                                    1 CTL-KV MOVE
1                                    1 CTL-KH UN BL
1                                    1 CTL-G DEL 1
1                                    1 CTL-Y DEL LN
1                                    1 CR ADD I LN
1                                    1 CTL-KX STOP
                                       CTL-KA SW

PG # 1   LINE 1   CURSOR 1   SPACE 1   LENGTH 1   # LINES 0

PATIENT # 1 JOE SMITH
```

FIG. 7

┌────────────────────────────────────────────┐
│ DO YOU WANT TO CORRECT THIS ONE? Y/(*)N?   │  Y
└────────────────────────────────────────────┘

FIG. 8

┌────────────────────────────────────────────────┐
│ SELECT A HEADER NUMBER OR [CR] TO DELETE THE TEXT. │  1
└────────────────────────────────────────────────┘

FIG. 9

```
THIS IS NUMBER TWO (2).
THIS IS NUMBER FIFTY ONE.  (51)
THIS IS NUMBER FIFTY ONE.  (51)

DO YOU WANT TO ADD TO THIS ONE? Y/(*)N?
```

FIG. 10

```
1  02/02/91                    PATIENT # 1 JOE SMITH

ENTER [CR] IF THIS OK OR [-1] TO TRY ANOTHER ONE.
```

FIG. 11

```
ARE YOU SURE THAT WANT TO DELETE THIS TEXT? Y/(*)N?
```

FIG. 12

```
THERAPY FILE DIRECTORY

1  CURRENT THERAPY DIET.
2  ADD TO THERAPY FILES.
3  UPDATE A THERAPY RECORD.
4  MEDICATION REFILLS.
5  CHANGE LONG TERM TO SHORT TERM THERAPY.
6  CANCELL A RECORD.
7  CORRECT THERAPY RECORDS.

SELECT ONE OR [CR] TO STOP  1
```

FIG. 13

```
PATIENT # 1   JOE SMITH

THE CURRENT DIET.
WATERCRESS SANDWICHES.

ENTER NEW DIET DESCRIPTION OR [CR] TO SAVE.

THE NEW DIET IS ENTERED HERE. . . . . . . . . . . . . . . .
```

FIG. 14

```
PATIENT # 1   JOE SMITH

THE CURRENT DIET.
WATERCRESS SANDWICHES.

ENTER NEW DIET DESCRIPTION OR [CR] TO SAVE.

THE NEW DIET IS ENTERED HERE

IS THIS OK? (*) Y/N?   Y
```

FIG. 15

```
ENTER RECORD NUMBER TO BE UPDATED OR [CR] TO END.    1
```

FIG. 16

```
           PATIENT # 1   JOE SMITH
DRUG   IRON VITAMINS AND MINERALS TABLETS 60 MG.
CURRENT DOSAGE 3

NEW DOSAGE:         6
         UPDATE              022191

IRON VITAMINS AND MINERALS TABLETS 60 MG.
```

FIG. 17

```
ENTER RECORD NUMBER TO BE CHANGED OR [CR] TO END.    1
```

FIG. 18

```
PRES #    123
DRUG #    TIMOLOL MALEATE TABLETS
PATIENT # 1    JOE SMITH

CURRENT REFILLS ALLOWED  2

ENTER NEW REFILL DATE   060191 [CR] IF NO REFILL.
```

FIG. 19

```
ENTER RECORD NUMBER TO BE CORRECTED OR [CR] TO END.
```

FIG. 20

```
CURRENT RECORD #  1

1  REFERENCED HEADER              11  HOSPITALIZATION LIST:
  2  PRESCRIPTION #.                223
  3  DOSE.                          45MG
  4  INITIAL DATE                   06/01/91
  5  REFILLS                        2
  6  GROUP #.  SHORT & PREVIOUS:    8
  7  UPDATE DATE                    05/27/91

SELECT ONE TO CORRECT OR [/] FOR THE NEXT RECORD OR [CR] TO END.
```

FIG. 21

```
PATIENT # 1    JOE SMITH

1  ADD A NEW LAB REPORT.
2  CORRECT AN EXISTING RECORD.

SELECT ONE OR [CR] TO END        1
```

FIG. 22

```
LAB TEST CATAGORIES.

1  BLOOD
2  CAVITARY FLUIDS
3  FECES
4  SPINAL FLUIDS
5  URINE

SELECT ONE OR THESE [CR] TO END    1
```

FIG. 23

```
ENTER TEST NAME OR [CR] TO END    CODEINE
```

FIG. 24

```
NEUROPSYCHIATRIC MEDICATIONS
BLOOD LEVELS:  GENERAL ANALGESICS

1  DATE:———
2  NOTES:———
3  NOTES:———
4  LAB #———
5  ACETAMINOPHEN———
6  CODEINE———
7  MEPERIDINE (DEMEROL)———
8  METHADONE (DOLOPHENE)———
9  MORPHINE———
10 PHENACETIN———
11 PROPOXYPHENE (DARVON)———
12 SALICYLATES———

TYPE [/] FOR NEXT SELECTION OR [CR] TO CONTINUE.
```

```
NEUROPSYCHIATRIC MEDICATIONS
BLOOD LEVELS:  GENERAL ANALGESICS

1  DATE:———01/15/91
 2  NOTES:   THIS IS A NOTE PERTAINING TO THIS TEST.
 3  NOTES:   THIS IS A SECOND LINE FOR NOTES.
 4  LAB #———                  1      THIS LAB IS NOT LISTED:
 5  ACETAMINOPHEN———                 ..... 15 STD      ............
 6  CODEINE———                12     ..... 15 STD 14   ............
 7  MEPERIDINE (DEMEROL)———          .....
 8  METHADONE (DOLOPHENE)———
 9  MORPHINE———
10  PHENACETIN———
11  PROPOXYPHENE (DARVON)———
12  SALICYLATES———

SELECT ONE TO CORRECT OR [CR] TO STOP.
```

```
 1  DATE:———
 2  NOTES:———
 3  NOTES:———
 4  LAB #———
 5  ACETAMINOPHEN———
 6  CODEINE———
 7  MEPERIDINE (DEMEROL)———
 9  MORPHINE———
10  PHENACETIN———
11  PROPOXYPHENE (DARVON)———
12  SALICYLATES———

TYPE [/] FOR NEXT SELECTION OR [CR] TO CONTINUE.
```

FIG. 27

```
NEUROPSYCHIATRIC MEDICATIONS
BLOOD LEVELS:  GENERAL ANALGESICS

1  DATE:————01/15/91
 2  NOTES:  THIS IS A NOTE PERTAINING TO THIS TEST.
 3  NOTES:  THIS IS A SECOND LINE FOR NOTES.
 4  LAB #————            1      THIS LAB IS NOT LISTED:
 5  ACETAMINOPHEN————                ..... 15 STD        ............
 6  CODEINE————          12     ..... 15 STD 14         ............
 7  MEPERIDINE (DEMEROL)————             .....
 8  METHADONE (DOLOPHENE)————
 9  MORPHINE————
10  PHENACETIN————
11  PROPOXYPHENE (DARVON)————
12  SALICYLATES————

SELECT ONE TO CORRECT OR [CR] TO STOP.
```

FIG. 28

```
LABORATORY FILE DIRECTORY

1  ADD A LABORATORY NAME
  2  CORRECT AN EXISTING RECORD
  3  PRINT THE CURRENT LIST.

SELECT ONE OR [CR] TO STOP  1
```

FIG. 29

```
           THIS ENTRY IS FOR LAB. NUMBER  6

1   LABORATORY NAME          KING LABS INC.
   2   ADDRESS                  123 ANY ST.
   3   CITY, STATE & ZIP        NAPA, CA  95456
   4   TELEPHONE                707/234/5678
   5   I.D. NUMBER              1234

ENTER NUMBER TO CORRECT OR [CR] TO CONTINUE.
```

FIG. 30

```
1  EASTERN LABORATORY               415/354/1212          12345
   347 SEVENTH ST.                        BERKELEY, CA  94611
2  SMITH KLINE                      //

3  JONES                            //

4  TTTTT                            //

5                                   //

6  KING LABS INC.                   707/234/5678           1234
   123 ANY ST.                           NAPA, CA  95456
[CR] TO CONTINUE
             DO YOU WANT TO PRINT THE LIST? Y/(*)N?   N
```

FIG. 31

```
LAB TEST HEADERS-FILE MAINTENANCE.

1  ADD OR CORRECT A RECORD.
   2  END THIS PROGRAM

SELECT ONE.   1
```

```
ENTER TEST CATAGORY NUMBER OR [CR] TO END.                    1
```

```
HEADER- 1    NEUROPSYCHIATRIC MEDICATIONS
HEADER- 2    BLOOD LEVELS:  GENERAL ANALGESICS
TESTING- 3
TESTING- 4
 DATE          DATE:
 NOTES:        NOTES:
 NOTES:        NOTES:
 LAB #         LAB #
TEST #1— 5   ACETAMINOPHEN
TEST #2— 6   CODEINE
TEST #3— 7   MEPERIDINE (DEMEROL)
TEST #4— 8   METHADONE (DOLOPHENE)
TEST #5— 9   MORPHINE
TEST #6— 10  PHENACETIN
TEST #7— 11  PROPOXYPHENE (DARVON)
TEST #8— 12  SALICYLATES
TEST #9— 13
TEST #10— 14
RECORD NUMBER 1&1.HDR

ENTER THE NUMBER TO CORRECT OR [CR] TO CONTINUE.
```

FIG. 34

```
LAST ENTRY   TIL1&37ELMS1&1 STUFF
TESTS-BLOOD. PG. #1

1  N.M.: BLOOD LEVELS: GENERAL ANALGESICS
 2  N.M.: BLOOK LEVELS: HYPNOTICS & SEDATIVES GROUP 1
 3  N.M.: BLOOD LEVELS: HYPNOTICS & SEDATIVES GROUP 2
 4  N.M.: BLOOD LEVELS: ANTI-EPILEPTIC MEDS: GROUP 1
 5  N.M.: BLOOD LEVELS: ANTI-EPILEPTIC MEDS: GROUP 2
 6  N.M.: BLOOD LEVELS: CNS STIMULANTS
 7  N.M.: BLOOD LEVELS: ANTI-ANXIETY MED.
 8  N.N.: BLOOD LEVELS: ANTI-DEPRESSIVE: GROUP 1
 9  N.N.: BLOOD LEVELS: ANTI-DEPRESSIVE: GROUP 2
10  N.N.: BLOOD LEVELS: ANTI PSYCHOTIC MEDS.
11  N.N.: BLOOD LEVELS: VARIOUS TYPES OF MED.
12  NON-NEURO. BLOOD LEVELS: CARDIOVASCULAR MED. GROUP 1
13  NON-NEURO. BLOOD LEVELS: CARDIOVASCULAR MED. GROUP 2
14  NON-NEURO. BLOOD LEVELS: CARDIOVASCULAR MED. GROUP 3
15  NON-NEUROPSYCHIATRIC: VARIOUS TYPES MED.

ENTER TEST CATAGORY NUMBER OR [/] FOR NEXT PAGE OR [CR] TO END.
```

FIG. 35

```
CURRENT FILE NAME 1&1
ENTER NAME REQUIRED OR [CR] TO END
```

FIG. 36

```
CURRENT FILE NAME 1&1
ENTER NAME REQUIRED OR [CR] TO END FASTER
CHANGE FILE HEADER NAME? Y/(*)N?
```

FIG. 37

```
KEY WORD DIRECTORY

1  ENTER NEW KEYWORD.
 2  CORRECT A KEYWORD
 3  PRINT THE KEYWORDS

ENTER ONE OR [CR] TO END
```

FIG. 38

```
THIS IS A NEW KEYWORD . . . . . . . . . . . . . . .
ENTER THE KEYWORD OR [CR] TO END THE INPUT
```

FIG. 39

| KEYWORD ALPHA LIST | | PAGE # 1 |
|---|---|---|

| | | |
|---|---|---|
| 74 | AV CONDUCTION DELAY | |
| 21 | CLOROX DERMATITIS | |
| 6 | HVD | |
| 4 | PVC'S | |
| 77 | THIS IS A NEW KEY WORD | |
| 35 | ABDOMEN PROTUBERANT | |
| 70 | ABDOMINAL PAIN | |
| 64 | ACUTE MYCARDIAL INFARCTION | |
| 23 | AMNESIC EPISODES | |
| 30 | ANOREXIA | |
| 25 | ANTRAL GASTRITIS | |
| 33 | ATELECTASIS | |
| 48 | BACK PAIN WITH PAIN DOWN RIGHT LEG | |
| 49 | BACK PAIN WITH PAIN DOWN LEFT LEG | |
| 27 | BILATERAL OOPHORECTOMY | |
| 63 | BLOOD TRANSFUSION | |
| 9 | BLURRING OF VISION | |
| 62 | BRUIT LEFT CAROTID | |
| 61 | BRUIT RIGHT CAROTID | |
| 46 | BURNING ACROSS UPEER ABDOMEN | |
| 45 | BURNING OF SKIN OF THIGHS | |
| 11 | CAROTID BRUITS | |
| 18 | CATARACTS | |
| 58 | CHRONIC FATIGUE | |
| 47 | CONSTIPATION | |
| 5 | CORONARY INSUFFICIENCY TYPE CHEST PAIN | |
| 59 | DECREASE IN HEARING | |
| 12 | DEEP VEIN THROMBOSIS | |
| 42 | DEGENERATIVE CHANGES, SPINE | |
| 43 | DEOSSIFICATION | |
| 51 | DIVERTICULITIS | |
| 7 | DIZZINESS | |
| 23 | DUODENITIS | |
| 44 | ESOPHAGEAL STRICTURE | |
| 8 | FAINTING | |
| 37 | FATTY INFILTRATION LIVER | |
| 68 | HERPES | |
| 13 | HIATUS HERNIA | |
| 22 | HYPERLIPIDEMIA | |
| 24 | HYPOKALEMIA | |
| 20 | HYSTERECTOMY | |
| 54 | LEFT KNEE PAIN | |
| 16 | LOW BACK PAIN | |
| 17 | MIGRAINE | |
| 75 | MITRAL LATE SYSTOLIC CLICK | |
| 69 | MITRAL VALVE PROLAPSE | |
| 41 | NARROWING SIGMOID | |
| 2 | NEUROLOGIC SYMPTOMS ASSOCIATED WITH HYPERTENSION | |
| 1 | NEUROLOGIC SYMPTOMS ASSOCIATED WITH TACHYARRHYTHMIAS | |
| 53 | NIGHT SWEATS | |
| 52 | NOCTURIA | |
| 50 | NODULARITY BREASTS | |
| 67 | OLD LEFT HEMIPLEGIA | |
| 73 | ORTHOSTATIC HYPOTENSION | |
| 38 | PANCREATIC CYST | |
| 65 | PARESTHES | |

FIG. 40

ENTER CORRECT KEY WORD OR [CR] IF THIS IS OK
NEUROLOGIC SYMPTOMS ASSOCIATED WITH TACHYARRHYTHMIAS
..................................................

FIG. 41

DO YOU WANT TO PRINT THIS (*)Y/N?

FIG. 42

DO YOU WANT TO PRINT ONE HEADER? Y/(*)N?

FIG. 43

ENTER HEADER NUMBER REQUIRED OR [CR] TO STOP.

FIG. 44

PRINT EXTRACTIONIST PROBLEM LIST? Y/(*)N?

FIG. 45

DO YOU WANT TO PRINT THIS? Y/(*)N?

FIG. 46

COMPUTERIZED FILE MAINTENANCE SYSTEM FOR MANAGING MEDICAL RECORDS INCLUDING NARRATIVE REPORTS

BACKGROUND OF THE INVENTION

A microfiche Appendix containing two microfiche and 152 frames was submitted as part of this application.

This invention relates to data processing by computer, and in particular relates to a computer application program for a system of file maintenance that is adaptable to small office computers such as the class of computers generally known as personal computers. The program is also useable on mini and mainframe computers for managing large record systems of hospitals or public agencies.

This invention is especially useful for client or patient records that must be constantly updated with narrative dictations as well as more easily classifiable data such as prescriptions and laboratory results. The file maintenance system is structured with data files with each file having a record set with the records in the set having fields for lodging specific information with some fields being of a hybrid-type allowing periodic amendment by deleting part of, or adding to, existing data without reentry of the existing data. In this manner the file structure is ideally suited for situations where long narratives must be broken-up into select categories and added or spliced into existing categorical report records.

The structure of the file system includes conventional field-defined data such as name, address, and telephone number which are ideally suited to conventional, field-defined records, where updated information wholly replaces existing information. The file maintenance system also includes the hybrid fields which allows lengthy narratives to be included as field data in a word processing style format. Adding, deleting or changing sentences, sections or words is accomplished in the same manner a word processed document is edited.

Previous record generator and maintenance programs are ineffective in handling records that include narrative reports as well as form-style data, particularly where amendments to the narrative reports must be added or spliced into existing data strings.

There are two basic types of computer programs that are in common use in the modern micro and mini computers. The first and most common is a program that stores, retrieves and processes the stored information. These programs use files that are commonly called data files. Data files usually have user defined names and normally are either of a fixed record length or dynamically allocated. Each record in a file will usually consist of one or more fields each one of a specific character length or separated typically by a comma. The size of these records are usually controlled either by the size of each field or the record length specified in the program. This is done to conserve space in the computer storage area particularly when many thousands of records are needed and where searching and sorting of files is required. The smaller the record the faster data can be accessed.

The above type of data file is used to store information such as customer records giving the names, address, and phone numbers etc. for each customer. Each field of this record can be either an alphanumeric string or a numeric field consisting of a real or integer number, or both.

When a user accesses a particular file and reads a certain record the user can display the contents of that record on the screen or print it with a printer. If necessary, the data in each of these fields can be changed by reentering data in a particular field and printing the fields back into the same record. The difficulty is, the user must retype the entire field to make the changes. The user cannot just edit or change one or more individual characters to obtain the desired effect of an amendment or correction.

The second type of program that is extensively used is called a word processor. This program is used to produce printed documents such as a letter. It produces a finished document that has all of the attributes such as margin control, indents paragraphs, file formats etc., all specified by the operator. There are many different programs of this type available and there are many features available.

A word processor program basically provides a record for each document in which the name of this document is user defined. The record generally consists of one field which can be of indeterminate length, with some practical limits. The information in this field is treated as one string, and characters are added or deleted as required to create a finished or correct document.

All control characters required by the program are embedded in this field and do not show in the printed text.

In a word processor system information in a particular document is not available except when a document is searched for a particular word. Except for header information, word processor files cannot be readily used for data processing.

The present invention is a program that utilizes data files but allows the reading of a particular record or combination of records in a file and allows the reader to make changes and corrections in an existing record. These records have report fields that are sufficiently large to make it impractical to retype the entire record as in a standard field defined record. Specifically, we make reference to a medical and dental records system where each record can be a categorical report several pages long. While the term, report, has special meaning in computer parlance, applicant here uses the term in its more general sense as a detailed account or statement.

The records in the system include category and date information plus other methods of differentiation from one to the other, permitting each information record to be sorted, retrieved, printed and corrected all in the same program. All of this takes place in the same file in a multi-file, records keeping system.

This program allows one to store large files in a data file environment yet one can manipulate the records in the files as required, using a word processor or editor environment on large, hybrid fields or, for certain formatted records, data reentry in standard fields for limited data entry.

SUMMARY OF THE INVENTION

The file maintenance system of this invention is applicable to record keeping where existing records are to be amended or updated and it is desired to process entered data to extract information in a manner similar to field defined data in a database. The unique feature of this invention is the combination of standard field defined record structures with hybrid, extended field records which are akin to word processing documents that permit editing without reentry of the data in the extended field. The field size of the hybrid field is designed to permit long narratives to be incorporated into the file and has particular applicability where a narrative is broken into selected categorical narrative reports which develop over an extended period of time.

For example, in an update of a patient's medical records, where a patient's visit prompts additions to his prescription file (or record) as well as a change of address and an update on the progress of a particular ailment, it is beneficial that the physician's comments or report be broken into various sections for entry into predefined file categories for digital storage and retrieval. On review, the physician can instantly go to the category of interest and review the file history of that category.

Modern medical practice has led to the technique of dictating patient reports that are subsequently transcribed, in some cases by professional transcribing agencies, for insertion into the patient's file of medical records. As medical practice moves toward the paperless office, with more records retained in digital databases for ease of access and minimization of physical storage, new methods are required to store such information in a format that is convenient to retrieve and review and yet maintains the integrity of the record.

The record keeping system of this invention meets these demands allowing the physician the convenience of dictating his reports for a transcriber who then extracts the pertinent sections of the dictated report for insertion into a set of predefined categories for convenient referral and use.

Since patient records are cumulative in nature, the extracted material can be appropriately added to, or even spliced into the middle of existing material. For medical applications in particular, the transcriber or extractionist, often called an abstractionist in medical parlance, includes a complete archival copy of the dictated narrative in the patients' records as a reference that can be accessed if necessary.

In the preferred embodiment the extracted material can be retrieved, displayed, edited and printed by a variety of link commands that are provided by screen prompts.

In contrast, the archival records are not customarily shown or printed when showing or copying a patient's records and are retrieved only by special access, to minimize the useable file size and retrieval time of the more useful working records.

As indicated by the examplar clinical systems format and outline used to describe the preferred embodiment, the above programs allow one to combine a therapy flow chart system, lab reports, patient history, prescriptions record and extractionist files in the same program.

One of the prime benefits derived from this method is that when additions or changes are made in a particular area it will only require the reprinting of the category header that was updated, avoiding the need to reprint the entire document such as in a word processor program. This is a very efficient use of the extractionist time and reduces computer time to a minimum.

The therapy files and lab reports are sorted by category and each entry indicates to which header it is related. Every entry in the system is available by category and date. Additional codes allow macro searching of these records for specific items, for example, by key words for locating such things as various types of cancer or skin diseases, where all patient files in the system are scanned for this particular information. This cannot be done with a word processor type of record system. This type of search can be done in a regular data file system but the medical narrative files are not present in conventional data file systems.

This invention comprises a unique method of combining two types of computer programs to allow the efficient use of the computer for medical or other record keeping.

The invention will primarily be described with reference to screen prompts which establish the user interface and the workings of the program. The program is written in basic and microfiche of the source code is submitted contemporaneously herewith as an appendix and is available as a patent and trademark office document.

BRIEF DESCRIPTION OF THE DRAWINGS

FIG. 3 is an extraction file directory screen display.

FIG. 4 is a prompt command screen display.

FIG. 5 is a header directory screen display.

FIG. 5a is a continuation of the header directory screen display of FIG. 5.

FIG. 6 is a header prompt screen display.

FIG. 7 is a header record screen display.

FIG. 8 is a prompt command screen display.

FIG. 9 is a prompt command screen display.

FIG. 10 is a prompt command screen display.

FIG. 11 is a prompt command screen display.

FIG. 12 prompt command screen display.

FIG. 13 is a therapy file directory screen display.

FIG. 14 is a therapy file record screen display.

FIG. 15 is a modified therapy file record screen display.

FIG. 16 is a prompt command screen display.

FIG. 17 is a side therapy record screen display.

FIG. 18 is a prompt command screen display.

FIG. 19 is a modified therapy file screen display.

FIG. 20 is a prompt command screen display.

FIG. 21 is a modified record screen display.

FIG. 22 is a add report prompt screen display.

FIG. 23 is a lab test category screen display.

FIG. 24 is a prompt command screen display.

FIG. 25 is a lab test screen display.

FIG. 26 is a modified lab test screen display.

FIG. 27 is a lab test screen display.

FIG. 28 is a modified lab test screen display.

FIG. 29 is a laboratory file directory screen display.

FIG. 30 is a laboratory file record screen display.

FIG. 31 is a laboratory list screen display.

FIG. 32 is a lab test file maintenance screen display.

FIG. 33 is a prompt command screen display.

FIG. 34 is a lab test screen display.

FIG. 35 is a lab test screen display.

FIG. 36 is a prompt command screen display.

FIG. 37 prompt command screen display.

FIG. 38 is a key word directory screen display.

FIG. 39 is a key word prompt command screen display.

FIG. 40 is a key word listing screen display.

FIG. 41 is a prompt command screen display.

FIG. 42 is a prompt command screen display.

FIG. 43 is a prompt command screen display.

FIG. 44 is a prompt command screen display.

FIG. 45 is a prompt command screen display.
FIG. 46 is a prompt command screen display.

DESCRIPTION OF THE PREFERRED EMBODIMENTS

The file maintenance system of this invention is particularly adaptable to a system for maintaining medical records. The unique problems that are involved in organizing and updating medical records require solutions having flexibility that is not generally encountered in most record keeping situations. However, the system has applicability whenever the records are not simply archival in fashion but when the records need to be periodically updated with narratives that are extracted into usable portions that relate to different topics. In such situations, a system that allows data-fields to be altered in the manner of a word processing document is extremely useful where the user may wish to compile information relating to one or more topics in the manner of a relational-type database.

The preferred embodiment described in this detailed description, is directed toward a medical record keeping system that maintains the records in a computer database for convenient and rapid access by the physician or others who require patient information. It is to be understood that the system can be adapted to any record keeping database where the needs may be similar, for example most situations where client interviews or other information is obtained that is not easily organized in conventional computer data systems. The file maintenance system of this invention is particularly useful where client or patient interviews are recorded on magnetic dictating equipment for subsequent transcribing by a transcriber who extracts selected topical information for inclusion in a categorically divided data file.

In general the file maintenance system of this invention devised for computer processing of multiple files of a client/patient type where periodic professional consultations with the client or patient results in new information that must be incorporated into a file that may include multiple categorical problem areas or topics. Because typical client/patient consultations result in narrative reports with various parts relating to various categorical topics, the file maintenance system of this invention has been designed to include record sets in an organizational structure having both a plurality of standard categorical, field-defined records with identified text fields of fixed character length for economy of storage and efficiency of access, and, a plurality of hybrid, categorical extended-field records of virtually unlimited character length enabling entry of narrative text reports. The text reports may be entered in complete, unedited archival form and duplicated and edited into separate, divided, subreports for entry into topical categories to facilitate review of client/patient file histories on select topics. The subreports or abstracted narratives in the topical categories can include readily identifiable key words entered into key word file for prompting fast access to particular clients or patients and the particular entries containing such key words.

Figure 1:
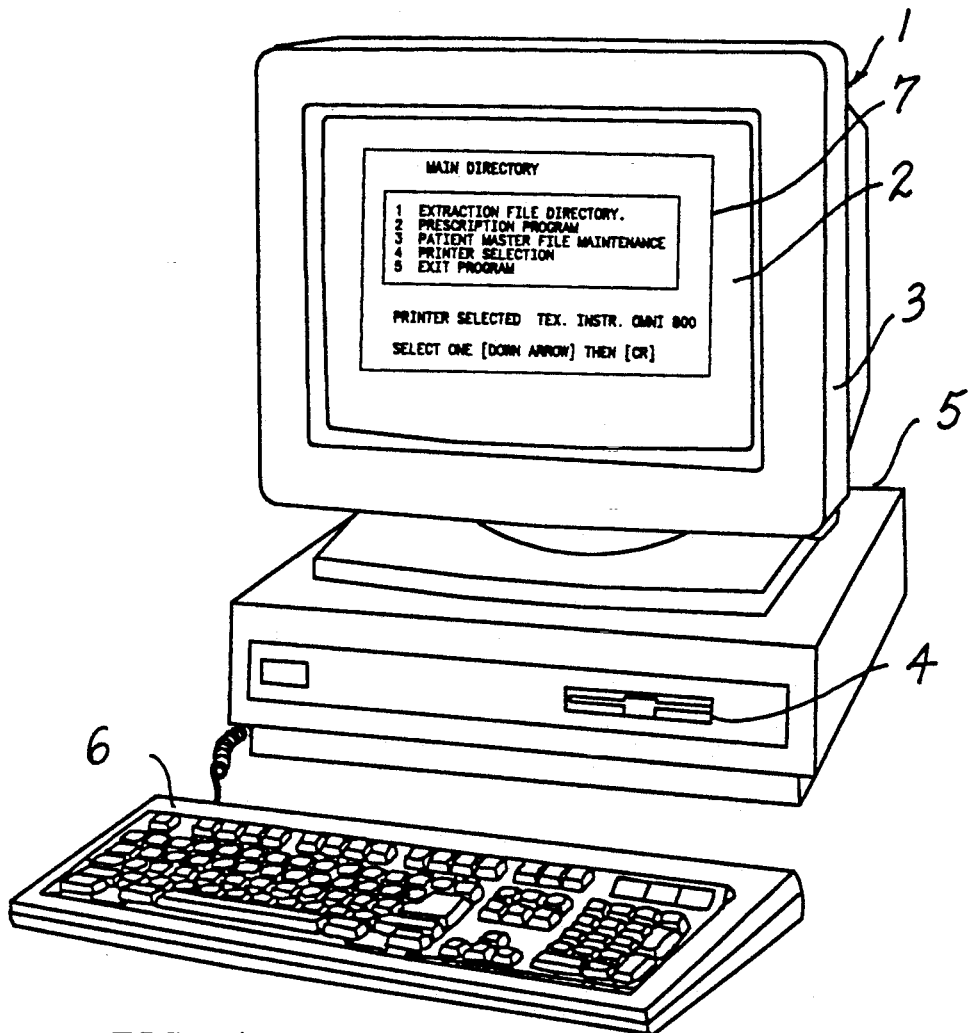
FIG. 1 is a perspective view of a computer system with a main directory screen display.
Figure 2:
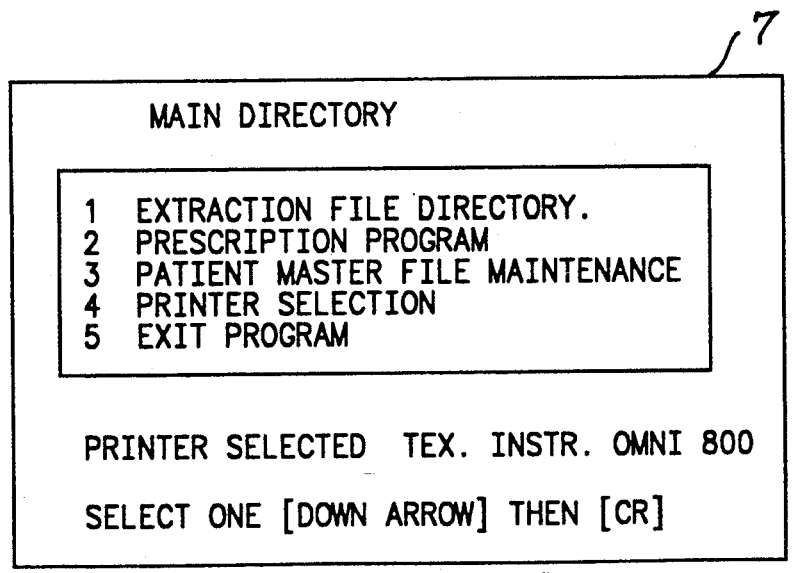
FIG. 2 an enlarged view of the main directory screen display.

To aid in the description of the file system, a walk through the various menu prompts that appear on the screen to aid the user will best describe the nature and content of the computer program. It is presumed that the user is using a conventional-type, personal computer system 1 that organizes application programs in various directory files that are displayed on a screen 2 of a monitor 3 that is part of the computer system 1 shown in FIG. 1. The user installs the program in a slot 4 in the processor 5 and opens the directory file using a keyboard 6 and is presented with a screen display 7 showing the main directory having four selections as shown in the screen 2 of FIG. 1 and in the enlarged screen display 7 of FIG. 2 The screen displays throughout this description are identified by the reference numeral 7.

The main directory lists five choices for the user. The extraction file directory selection will open the extraction files for review or update. The prescription program selection will open a data-base of common drugs and medications for which the physician can select an appropriate therapy regimen. The patient master file maintenance selection will open a data-base of the patient roster that includes key information to identify the patient and locate the patient file number. The printer selection will open a preference routine for selection of an appropriate interface command for the particular brand of printer that is coupled to the computer processor being used for the file maintenance system. The exit program will result in exiting the program.

When the extraction file menu selection is activated, the extraction file directory is then displayed as shown in FIG. 3. When the user wishes to add to extraction files, the appropriate identification number is selected and the user is prompted to enter the patient's name or his file number as shown in FIG. 4 with a prompt verification also as shown in FIG. 4. A series of categorical headings are then displayed as shown in FIG. 5, as continued in FIG. 5a, and the user is prompted to request one of the selected categories for entry of the new material. Where the entry is a physician's narrative that must be broken into subsections for inclusion into one or more defined header categories, the usual practice is to first enter the complete narrative into category 51, Progress Notes, together with the date of the entry as shown in FIG. 6. From there, selected information is extracted and entered under another header or under a newly defined header. The original entries of the progress notes in header 51 are retained as an archival copy and are usually not printed when printing the records of a patient unless a special command is entered.

After the header number is selected the header information directory will be displayed as shown in FIG. 6. The date is the current date which is entered automatically and provides a logging tool for verifying entries in the archival copy retained under the Progress Notes, header. Key words are normally not used in the Progress Notes category. After typing ENTER to proceed to the entry mode, the new text or transcription can be entered. During and after entry all corrections and additions can be made with the control codes, which are patterned after conventional text-based control editing features of conventional word processor applications.

The word processor commands that are utilized compare with early text-based commercial word processor programs. The control characters for editing narrative reports are as follows:

Cursor Controls

CTL-C = Down One Page.
CTL-R = Back One Page.
CTL-D = Move Cursor 1 Space to the Right.
CTL-F = Move Cursor 1 Word to the Right.
CTL-S = Move Cursor 1 Space to the Left.
CTL-A = Move Cursor 1 Word to the Left.

CTL-N=Move Cursor to the End of the Text.
CTL-0=Move Cursor to the End of the Page.
CTL-B=Move Cursor to the Beginning of the Text.
CTL-T=Move Cursor to Beginning of Page.
CTL-E=Move Cursor Up One Line.
CTL-X=Move Cursor Down One Line.
Tab=Move Cursor 5 Spaces to the Right.
Enter [CR]=Add a Line and Move Cursor to Beginning of Next Line.

Editing Functions

CTL-KB=Mark Start of Block.
CTL-KK=End of Block.
CTL-KV=Copy Block to Another Section.
CTL-KH=Remove Blocks.
CTL-G=Delete the Character at the location of the cursor.
CTL-Y=Delete the Line containing the cursor.
Backspace=Delete Next Left Character and Move the Cursor Back One.
CTL-KX=End The Entry and Return to the Directory.

The steps for adding to the extraction files are as follows:

HOW TO ADD TO THE EXTRACTION FILES

1. To change the directory to [md], type "cd/md" then "return".
2. After the user has selected #1 in the extraction file directory he will have to enter either the patient's number or name as prompted in FIG. 4. If the user entered the patient's last name, the next step will be to type in first name or initial. If there are similar names such as "Ruth Brown, Rob Brown, or Roy Brown" the user types "enter" until the correct one appears, FIG. 4. Of course, the quickest and most accurate way is to type the patient number that is shown on the patient file which will eliminate a similar name or spelling problem. After the user has approved the patient's name FIG. 4 the various specified headers will be displayed FIG. 5-5a. Any of the others may be selected when there is a need to add a new header paragraph directly. The normal routine is to use the "51" then extract and move the information from there to other headers or a new header. Header #51 saves the complete transcript for the archival storage.
4. After the header number is selected the header control information directory will be displayed, FIG. 5. The date is the current date which is entered automatically and the header number is the one that has just been selected. In addition, the keyword should be entered at this time. The keyword is not used in #51 progress notes. All three items can be changed if necessary at this time, or the user types "/" and "enter" to stop, FIG. 5.
5. To proceed to the entry mode for the new header paragraph the user types "enter".
6. The next step is to type in the new text or transcription.
7. During and after entry, all corrections and additions can be made with the control codes as described in softmed.doc or as displayed on the screen, FIG. 7. Ctl-k is typed to terminate the entry and return to the header entry display, FIG. 5. If no further action is required enter −1 to return to extraction file directory, FIG. 3.

It is customary that the extractionist who transcribed and entered the dictated progress report of the physician into the Progress Notes category, would then extract appropriate selections for placement into the subject categories of the designate patient's file. The subject categories are listed in FIG. 5. It is to be understood that the category headers would differ for other client bases, for example, for dental patients or legal clients.

The separation of the entered progress report into specified categories enables consolidation of those comments or common topics to facilitate review. For medical patients this is particularly useful since many years of a patient's life may be tracked with recurrent problems in a continuing ailment. Referral back to this problem area instead of sifting through the complete file is not only timesaving, but prevents something from being overlooked. The steps for correcting and moving text in the extraction files are as follows:

HOW TO CORRECT AND MOVE TEXT IN THE EXTRACTION FILES

1. To extract from the progress notes, the user selects #2 in the extraction file directory, FIG. 3.
2. Next the user selects and approves the patient required, FIG. 4.
3 The header selection will then be displayed, FIG. 5 then "/" is typed to page through the lists. If the desired header is missed the user can start over. The highlighted chevrons at the right side of the display indicated headers that are being used in the current patient file. "Return" is typed before entering the desired header number.
4. Each paragraph that exists for the selected header will be displayed one after the other with a prompt FIG. 8. By entering "n" the next paragraph will be displayed. The user repeats this procedure until the desired paragraph is found. By entering "y" the selected header information will be displayed, FIG. 6.
5. If only the header information is to be changed the user now makes the changes, then the user can terminate at this time by typing "/" and "enter".
6. When the user wants to proceed with correcting the selected paragraph, he types "enter" and the paragraph will be displayed, FIG. 7. Then, the user can proceed with the correction routine using the editing commands. If the user is copying text, the beginning of the text is marked with "ctl-kb;" and the end of the text "ctl-kk". The user then types "ctl-kv" to move the selected text, or types "ctl-kx" to terminate the edit at this time.
7. The selected text is displayed, FIG. 7. The user determines whether or not it is desired that the text be added to an existing paragraph or a new paragraph is to be created. Type the header number for the new paragraph or the paragraph to which the text is to be added, FIG. 9.
8. When a user is adding to an existing header, the first paragraph of the selected header will be displayed FIG. 10. The user types "n" to select the next paragraph under this header. This step is repeated until the user has the correct paragraph or types "enter" to stop FIG. 11.
9. If the user answered "y" the finished paragraph will be shown for final approval or rejection, FIG. 11.
10. If the entry is approved the user types "enter" and the extraction directory will be displayed in FIG. 3, or the user types "−1" to restart.

If the option in FIG. 9 is to delete the marked text by typing "enter," there will be an opportunity to reject that option, FIG. 12.

If the text is deleted, the screen will return to extraction file entry mode, FIG. 5. At this point type "−1" to stop the correction mode.

In a similar manner the patient's diet or therapy regimen may be tracked and updated by entering #6, 7, 8, or 9 in FIG. 5. Alternately, the following correction mode can be used.

HOW TO UPDATE A THERAPY FILE DIET

1. Select #3 in the extraction file directory, FIG. 3
2. Select and approve a patient file, FIGS. 4.
3. The therapy file directory will be displayed, FIG. 13.
4. Type #1 and the current diet will be displayed, FIG. 14. Approval is required, FIG. 15. Then the user can return to therapy file directory, FIG. 13.

The data records in the flow chart file are specified field entries and unlike the narrative records of the extraction files, the records are edited by replacement of the entries in the designated fields. The additions, changes, or updates to a therapy file or the medication prescription are performed by the following steps under the appropriate headings:

HOW TO ADD A NEW THERAPY FILE

1. If a user wants to add a new therapy record he types "2" in the therapy file directory and "enter" FIG. 13
2. The therapy input header will now appear, FIG. 15.
3. Each input item will automatically appear for input.
4. While entering the next six items the user can return to the previous entry by simply typing "r" and "enter" then the last input request will be repeated.
5. The first input item will ask for the referenced header as specified by the physician. The user types "enter" if there is no input.
6. The user enters the prescription code (see master prescription file) for the prescription specified by the physician. This is required.
7. The user enters the dosage prescribed by the physician.
8. The user enters the number of refills permitted.
9. The user enters the date that this is issued to the patient.
10. The last entry allows three options, one for long-term therapy one for short-term therapy and one for previous therapy.
11. After all entries are completed the user will have the opportunity to correct any of these items simply by typing in the corresponding number and making the corrections.
12. After all corrections are made the user types "enter" to return to the therapy file directory, FIG. 13.

HOW TO UPDATE A THERAPY FILE RECORD

1. When an existing long-term therapy is to be updated the user selects #3 in the therapy file directory, FIG. 13.
2. The record number will be requested, FIG. 16. The user then refers to the number in parenthesis following the date on the patient's printed therapy report.
3. The new dosage and date is entered as required, FIG. 17.
4. Any necessary changes are made at this time. To return to the therapy file directory FIG. 13, "enter" is typed.

HOW TO DO A MEDICATION REFILL

1. To perform a medication refill, #4 in the therapy file directory FIG. 13, is selected.
2. The record number will be requested, FIG. 18. The user must refer to the number in parenthesis following the date on the patient's printed therapy report.
3. The user types in the "new date" and "enter" FIG. 19, or if ok or no change he types "enter" to return to the therapy file directory, FIG. 13.

HOW TO CHANGE A LONG-TERM THERAPY FILE TO PREVIOUS THERAPY

1. To change long-term to the user selects #5 in the therapy file directory, FIG. 13.
2. The record number will be requested, FIG. 18. The user must refer to the number in parenthesis following the date on the patients' printed therapy report.
3. No further input will be required and the user will be returned to the therapy file directory, FIG. 13.

HOW TO CANCEL AN EXISTING THERAPY RECORD

1. To cancel a record the user selects #6 in the therapy file directory, FIG. 13.
2. The record number will be requested, FIG. 20. The user must refer to the number in parentheses following the date on the patient's printed therapy report.
3. No further input will be required. The user will be returned to the therapy file directory, FIG. 13.

HOW TO CORRECT AN EXISTING THERAPY RECORD

1. Enter #7 in the therapy directory, FIG. 13.
2. The user enters the record number to be corrected, FIG. 20.
3. The corrections as required are made, FIG. 21.
4. The user types "enter" to return to extraction file directory, FIG. 3.

In a similar manner, the data files for laboratory reports are maintained by a format that provides fields for data entry. The procedure for maintaining the laboratory report file is as follows:

LABORATORY FILE MAINTENANCE

1. A user types #4 in the extraction file directory, FIG. 3.
2. The user selects and approves a patient file, FIGS. 4.
3. The lab input directory will appear, FIG. 22.
4. To add a new lab report, #1 is selected.
5. The laboratory category directory will appear, FIG. 23.
6. One of the five items is selected.
7. Next the test result name that is shown on the lab report is entered, FIG. 26.
8. If this name is proper the appropriate lab report header will appear on the screen, FIGS. 27. If this is not the correct header "/" and "enter" is typed and the next header that is in the same category will appear.

9. When the correct header appears on the screen then "enter" is typed to go to the input mode, FIGS. 28. The user types in the required information and makes any corrections necessary, then types "enter" to return to the extraction file directory, FIG. 3.

HOW TO ADD TO THE LABORATORY NAME LIST

1. Enter #6 in the extraction file directory, FIG. 3.
2. A user selects #1 in the laboratory file directory, FIG. 29.
3. The laboratory name, address, etx. , as required is entered, FIG. 30.
4. Repeat the above steps as many times as necessary.
5. The user types "enter" to return to the laboratory file directory, FIG. 29.

HOW TO CORRECT AN EXISTING LABORATORY FILE

1. The user selects #2 to correct an existing file FIG. 29.
2. Enter the code number of the laboratory record to be corrected.
3. The required changes are made, FIG. 30.
4. The user types "enter" to return to the laboratory file directory.

HOW TO PRINT THE LABORATORY LIST

1. A user selects #3 in the laboratory file directory, FIG. 29.
2. The prompted option is to either print the list on the printer or display the list on the screen, FIG. 31.
3. The laboratory file directory will thereafter appear, FIG. 29.

The software program can be updated and amended to include new templates for additional tests as warranted for the particular practice of the physician user.

LABORATORY HEADER MAINTENANCE

This program is used to create the laboratory input and output headers. There is one created for each set of laboratory reports.
1. A user selects #8 in the extraction file directory, FIG. 3.
2. The lab test header directory will appear, FIG. 32.
3. The test category is selected, FIG. 23.
4. Next, the test number is selected from those displayed, FIG. 33.
5. After the test is selected the proper header for this test series will be on the screen, FIG. 34.
6. The user types in all of the required information for each item, or make corrections as needed. The lab report headers prepared in advance by the physician, are entered at this time.

As a part of maintaining the laboratory test report file, a search word can be included in association with the header to enable access to data files in laboratory reports that may be helpful in determining commonality of problems or the like. This can be accomplished by the following procedure:

TEST SELECTION FILE MAINTENANCE

This program is used to add a particular search word for the data files used in laboratory result entry.

1. The user selects #9 in the extraction file directory, FIG. 3.
2. A user selects #1 in the laboratory test headers directory, FIG. 32.
3. The test category is selected, FIG. 23.
4. The test number is selected, FIG. 35.
5. The search word to be added to the data file is entered, FIG. 36.
6. The word entry may be repeated as often as necessary.
7. The options are to change the test number or the test category, FIG. 37, FIG. 23 and FIG. 35.
8. "Enter" is typed to return to the directory, FIG. 32.
9. "Enter" is then typed to return to extraction file directory, FIG. 3.

To enable the physician to have a cross link among patient records, a keyword index is maintained. This enables multiple patient records to be searched for common factors using keyword sorts and searches.

KEY WORD FILE MAINTENANCE

1. A user selects #7 in the extraction file directory, FIG. 3.

ADD A NEW KEY WORD

1. The key word directory will appear on the screen, FIG. 38.
2. The user selects #1 and "enter".
3. The user types in the "new key word" and repeats as many times as is necessary, FIG. 39.
4. "Enter" is typed to return to the key word directory, FIG. 38.

CORRECT A KEY WORD FILE

1. A user selects #2 in the key word directory, FIG. 38 to correct a keyword file.
2. The record number of the key word record is entered, from the printed key word list FIG. 40. The existing record is then displayed. The correction is made or "enter" is typed to pass FIG. 41.
3. The user types "enter" to return to the key word directory, FIG. 38.

PRINT THE KEY WORD LIST

1. A user selects #3 in the key word directory, FIG. 38 to print the key word file.
2. The prompted option is to either print the list on the printer or on the monitor, FIG. 42.
3. "Enter" is typed to return to the key word directory, FIG. 38.
4. "Enter" is then typed to return to the extraction file directory, FIG. 2.

To obtain a hard copy of a patient report or a part of the patient report the following procedure followed:

HOW TO PRINT A PATIENT REPORT

1. A user selects #5 in the extraction file directory, FIG. 3.
2. The user selects and approves a patient file, FIGS. 4.
3. The prompted option is to either print a single header or select one specific header for printing, FIG. 43.
4. If the user has elected to print a single header the header number is entered, FIG. 44. The only item printed will be the page for the header selected, otherwise, the entire file will be printed.

5. The next option is to bypass or print the header #51 or extractist problem file, FIG. 45.
6. The last option is to print this on the printer, otherwise it will print to the terminal, FIG. 46. One must be sure that the printer is on and that the paper is set.
7. The extraction file will appear on the screen, FIG. 12.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. In a computerized data processing system including a central processor with means for data storage, a keyboard for data entry and a screen display for data review, a file maintenance system for computerized processing of multiple files having record sets in a predefined organizational structure comprising:

a plurality of discrete files, each file having a plurality of records in a record set associated with the file, wherein the record set includes:

standard, field-defined records, each with an identified data field in which field-defined data of limited character length forming the field-defined record is enterable, the standard, field-defined records being organized in different field-defined categories in the record set, wherein the data processing system includes means for entering field-defined data in an identified data field of a field-defined record and means for editing field-defined data entered in the identified data field of the field-defined record by reentry of field-defined data in the data field; and, hybrid, extended-field records each with an identified data field in which extended-field data of virtually unlimited character length forming the extended field record is enterable, the hybrid, extended-field records being organized in different extended-field topical categories in the record set, wherein the data processing system included means for entering extended-field data in an identified data field of an extended-field record and means for editing extended-field data entered in the identified data field of the extended-field record without reentry of entered extended-field data in the identified data field.

2. The system of claim 1 wherein field-defined data in the form of text entered into the data fields of standard, field-defined records replaces field-defined data in the form of text previously entered into the data fields of the standard, field-defined records.

3. The system of claim 2 wherein the hybrid, extended-field records are documents, and wherein the computerized data processing system has editing features wherein data in the form of text is entered in data fields of hybrid, extended-field records without replacing data in the form of text previously entered into the data fields of the hybrid, extended-field records.

4. The system of claim 3 wherein the hybrid, extended-field records have extended-field topical categories including an archival category, and means for entry and storage of text narratives in the archive category and multiple, topical categories wherein complete text narratives are duplicated and subdivided into topical reports, each subdivided topical report being selectively entered into the topical category to which the topical report relates.

5. The system of claim 4 wherein entered archival text narratives have dated entries and the subdivided topical reports are dated on entry into the selected topical category.

6. The system of claim 5 wherein each topical category has a descriptive header and dated, subdivided topical reports are entered in each category according to the correlation of the topic of the subdivided report with the topic of the category.

7. The system of claim 3 wherein the file maintenance system includes command means for editing extended-field records in the manner of a conventional word processing document.

8. The system of claim 7 wherein the extended-field records include key words accessible by the command means.

9. The system of claim 1 wherein the plurality of discrete files of the file maintenance system are client/patient files, each file having a set of updatable records for a particular client/patient.

10. The system of claim 9 wherein the standard, field-defined records are primarily dedicated to client/patient identification data.

11. The system of claim 10 wherein the hybrid, extended-field records are primarily dedicated to client/patient progress narratives.

12. The system of claim 11 wherein the standard, field-defined records include a key word file.

13. The system of claim 11 including means to print standard, field-defined records and hybrid, extended-field records.

* * * * *